United States Patent [19]

de la Guardia et al.

[11] Patent Number: 4,605,018
[45] Date of Patent: Aug. 12, 1986

[54] METHOD OF TREATING HAIR AND ANHYDROUS COMPOSITION RELATED THERETO

[75] Inventors: Mario de la Guardia; Charles R. Hendrix, Jr., both of Savannah, Ga.

[73] Assignee: Carson Products Company, Savannah, Ga.

[21] Appl. No.: 517,709

[22] Filed: Jul. 27, 1983

Related U.S. Application Data

[63] Continuation-in-part of Ser. No. 236,118, Feb. 19, 1981, abandoned.

[51] Int. Cl.[4] .............................................. A45D 7/00
[52] U.S. Cl. ...................................................... 132/7
[58] Field of Search .............................. 132/7; 424/89

[56] References Cited

U.S. PATENT DOCUMENTS 2,261,094 10/1941 Speakman ................................ 132/7
4,324,263  4/1982 de la Guardia ......................... 132/7

OTHER PUBLICATIONS

226 USPO, pp. 51–57.
Cosmetics Science and Technology, 1957, Sagarin, pp. 461–462, 464–465, 467, 469.
Cosmetics Science and Technoloy, vol. 3, Second Edition, 1974, pp. 583–585, 597, 604–610.

*Primary Examiner*—Gregory E. McNeill
*Attorney, Agent, or Firm*—William H. Needle

[57] ABSTRACT

An anhydrous composition comprising an anhydrous emollient and an effective amount of a water-soluble guanidine salt together with an effective amount of a water-soluble inorganic oxide. Upon the mixing of an effective amount of water with the composition, guanadine hydroxide is formed which is used to treat the hair.

4 Claims, No Drawings

METHOD OF TREATING HAIR AND ANHYDROUS COMPOSITION RELATED THERETO

CROSS-REFERENCE TO RELATED APPLICATION

This is a continuation-in-part application of co-pending application Ser. No. 236,118, filed Feb. 19, 1981 now abandoned.

BACKGROUND OF THE INVENTION

This invention is an improvement over U.S. Pat. No. 4,304,244, issued Dec. 8, 1981; U.S. Pat. No. 4,324,263, issued April 13, 1982; and U.S. Pat. No. 4,373,540, issued Feb. 15, 1983 which disclose compositions and methods for treating hair wherein the compositions contain, as a principal active ingredient, guanidine hydroxide. The guanidine hydroxide is prepared by reacting a water-soluble inorganic hydroxide, such as calcium hydroxide, with a water-soluble guanidine salt, such as guanidine carbonate. The guanidine hydroxide composition is applied to the hair for a selected period of time to, for example, relax or straighten the hair. Thereafter, the hair may be rinsed and neutralized.

Guanidine hydroxide is rapidly converted, when in the presence of carbon dioxide, into guanidine carbonate, which is inactive as a hair treating agent. Furthermore, in the presence of moisture, the guanidine hydroxide decomposes into lower molecular weight compounds which are also inactive as hair treating agents. Thus, the guanidine hydroxide compositions are presently marketed in a two component system, with the guanidine carbonate being in one container, and the calcium hydroxide being in a separate container, the two container contents being mixed just prior to the hair treatment.

SUMMARY OF THE INVENTION

The present invention is directed to a stable composition which can be packaged in a single container and which, upon the addition of water, forms an aqueous composition which is suitable for treating hair to cause the hair to assume a desired configuration. It has been found that, so long as water is avoided in the stable composition, a guanidine salt and an inorganic oxide can both be present in the same composition without undue impairment of storage stability.

The guanidine salt and the inorganic oxide are selected such that the anion of the guanidine salt forms a substantially water-insoluble salt with the cation of the oxide. The guanidine salt includes guanidine carbonate, oxalate, tartrate and sulfate. The oxides include calcium, barium, strontium and mixtures thereof.

In addition to the guanidine salt and the inorganic oxide, the stable composition of the present invention also includes an anhydrous emollient to protect the scalp.

DETAILED DESCRIPTION OF THE INVENTION

The inorganic hydroxides which can be used in the present invention are barium hydroxide, calcium hydroxide, strontium hydroxide, or mixtures thereof. These hydroxides are water-soluble, and such solubility is required in order to produce the guanidine hydroxide when the stable composition of the present invention is incorporated into an aqueous medium. Availability, cost and effectiveness make calcium hydroxide the most preferred hydroxide. In view of the oral toxicity of barium hydroxide, the barium hydroxide is much less preferred than calcium hydroxide.

It appears that the reaction between the inorganic hydroxide and the guanidine salt is an equilibrium reaction, and if the anion of the guanidine salt does not form a substantially water-insoluble salt with the cation of the hydroxide, then the reaction to produce the desired guanidine hydroxide will not be driven towards completion. For this reason, it is critical that the anion of the guanidine salt form a substantially water-insoluble salt with the cation of the inorganic hydroxide. The salt produced by the reaction of the inorganic hydroxide and the guanidine salt should be more water-insoluble than lithium carbonate, but within this broad criteria, a large number of water-soluble guanidine salts can be used with the barium hydroxide, calcium hydroxide, strontium hydroxide, or mixtures thereof. The preferred guanidine salts are guanidine carbonate, guanidine oxalate, guanidine tartrate and guanidine sulfite, and of these guanidine carbonate is especially preferred. Other operable guanidine salts which can be used in the present invention include guanidine phosphate, guanidine fluoride, guanidine sulfate and guanidine laurate.

Various analogs of the above-mentioned guanidine salts, such as, for instance, guanidine bicarbonate, guanidine bisulfite, and guanidine bisulfate, can also be utilized. Of the guanidine salts listed above, the laurate, phosphate, sulfite and fluoride would be less preferred than those indicated to be among the preferred class. Furthermore, guanidine alginate may be used but takes considerable time to reach equilibrium pH.

When it is desired to form the aqueous hair treating composition, water is added with thorough mixing to the stable composition of the present invention, in an amount of at least approximately 3% by weight, based on the total weight of the aqueous hair treating composition to form an emulsion with the organic emollient, and the emulsion can be either the oil-in-water or the water-in-oil type (the former is preferred). Upon the addition of water, the inorganic hydroxide and the guanidine salt react together, and the reaction proceeds rapidly at substantially ambient conditions, although elevated or reduced temperatures could be utilized if desired.

When the guanidine salt and the inorganic hydroxide react together to form guanidine hydroxide, a rise in the pH of the composition will be noted. This pH rise can be measured with an appropriate pH indicator, if desired. The aqueous hair treating composition will normally have a pH value above 11.8 and preferably about 12.5 to about 13.5. The pH of the composition may rise above 13.5 within 24 hours after its preparation.

After the addition of water to the stable composition, with thorough mixing, the resulting hair treating composition should be used within about 48 hours, due to the relative instability of the guanidine hydroxide solutions exposed to ambient conditions.

It is greatly preferred that the inorganic hydroxide be present in at least a stoichiometric amount, based upon the amount of guanidine salt present in the stable composition. More preferably, the inorganic hydroxide is present in an amount equal to 2–5 times the stoichiometric amount, although this is not critical. Compositions containing the above noted amounts of inorganic hydroxide are generally above the hydroxide solubility level, so that amounts of hydroxide substantially in excess of the above range may be used without causing undue difficulties. However, the presence of too much inorganic hydroxide, such as calcium hydroxide, could form a gritty texture and might cause undesired deposits in the user's hair.

Less than stoichiometric amounts of the inorganic hydroxide may be used, but then the system will be less effective, and it is strongly preferred that an excess of hydroxide be used. Within these broad parameters, however, the amount of inorganic hydroxide used is not critical.

The active hair treating component of the aqueous hair treating composition is guanidine hydroxide (or guanidium hydroxide), and that compound tends to irritate the scalp of some users. To protect the scalp against such irritation, it is necessary to utilize an emollient in the stable composition. The emollient can be any of those emollients known to the art, such as lanolin products, petrolatum, mineral oil, cocoa butter, and the like. Normally, the emollient will be an oily organic compound which can form a physical barrier to prevent contact by too much guanidine hydroxide with the scalp of the user. As the formation of a emulsion is necessary, it is necessary to use an emulsifier, or else a self-emulsifying emollient. The nature of the emulsifier is not critical, as any of the emulsifiers normally used in cosmetic chemistry to form an emulsion of water and emollient can be used. Specific examples of emulsifiers are described in the examples below. It is preferred that the emulsifiers utilized in the compositions of the present invention have an HLB (Hydrophilic-Lipophilic Balance) number of 6.3 to 17. It is particularly preferred to utilize a combination of at least two emulsifiers, at least one having a high HLB number and at least one having a low HLB number, but wherein the combined HLB number is within the aforesaid range of 6.3 to 17. It has been found that these compounds give particularly favorable results.

The self-emulsifying emollients include Cyclochem NI, described in the examples below, as well as Arlacel 165 (ICI), a mixture of glycerol stearate and PEG-100 stearate.

When an emulsifier is utilized, the emulsifier should of course be compatible with the remaining ingredients of the composition of the present invention. In addition, for optimum commercial products, the emulsifier should be such as to quickly form the desired emulsion, while at the same time exhibiting ease of removal from hair at the time the composition is removed therefrom. Within these parameters, a wide number of emulsifiers can be utilized. Preferably the emulsifier is based upon one or more ethoxylated ethers, although propoxylated materials and capped ethers (that is, compounds wherein a combination of ethylene and propylene oxide is used seriatim) may also be used. Less preferred but still operable are ethoxylated, propoxylated and capped ester compounds. The stearate compounds are particularly preferred, although laural and cetyl derivatives are also operable. The lower melting point emulsifying waxes are preferred, expecially those compounds having from 2 to 60 moles of ethylene oxide per mole of monofunctional alcohol or acid.

The emulsifier will normally be used in an amount of from 0.5 to 30 weight percent, preferably from 10 to 20 weight percent. It is possible, of course, to use greater amounts of the emulsifier if desired.

Other conventional additives may also be present in the compositions of the present invention in order to provide their known functions therein. Such additional additives include thickeners, humectants, preservatives, accelerators, and the like.

Thorough mixing of the stable composition with water is strongly recommended. The reaction between the inorganic hydroxide and the guanidine salt, after thorough mixing, generally proceeds rapidly, and normally will be substantially complete within a few minutes or so. The reaction produces guanidine hydroxide and a water-insoluble salt, and the guanidine hydroxide in the aqueous solution tends to be converted to guanidine carbonate (which is inactive as a hair treating agent) upon exposure to atmospheric carbon dioxide, and tends to be degraded into lower molecular weight products upon exposure to water, so that the aqueous hair treating composition containing the guanidine hydroxide should be used in a freshly prepared condition—that is, within 48 hours of mixing the stable composition with water.

Higher concentrations of guanidine hydroxide in the aqueous hair treating composition raise the possibility of greater scalp irritation and more hair damage. The treatment time can generally be reduced with such higher concentrations, however, so that if adequate care is taken, as may be the case in commercial beauty shop operations, to minimize exposure, such higher concentrations may be utilized. In general, the amount of guanidine hydroxide in the aqueous hair treating composition of the present invention can vary from about 1% by weight to about 50% by weight, based on the total weight of the composition. Concentrations below about 1% by weight are generally too dilute to be effective, and concentrations of guanidine hydroxide above about 50% by weight generally exceed the solubility limit. It is greatly preferred that the guanidine hydroxide concentration be within the range of around 1.50% to 20% by weight, based on the total weight of the composition. More preferably, the guanidine hydroxide concentration is in the range of around 2.0% to 10% by weight, and most preferably the guanidine hydroxide concentration is from around 2.50% to 7% by weight, based on the total weight of the composition.

Normally the stable composition of the present invention will contain from 15% to 97.26% by weight of emollient. Thus, the composition will generally contain about 1.94% to 84.2%, preferably 3% to 13% by weight of the guanidine salt, 0.80% to 83.06%, preferably 1.25% to 15% by weight of the inorganic oxide, and 15% to 97.46%, preferably 78% to 95.75% of the emollient.

It will be readily appreciated that an increase or decrease in the concentration of one component may be compensated by appropriate adjustments to the concentration of the other ingredient, and to the ratio of the inorganic oxide and the guanidine salt in the final formulation. The important item is the concentration of the resulting guanidine hydroxide in the final aqueous hair treating composition, and that concentration should be within the ranges set forth above.

The time of treatment of hair to be relaxed or otherwise treated with the aqueous hair treating composition produced from the stable composition of the present invention will normally be within the range of 5 to 45 minutes, with the time starting from the first application of the hair treating composition to the hair. Generally the time of treatment will be at least 10 minutes, and there is no real upper limit on the time the composition can remain on the hair, so long as scalp irritation and/or hair damage is avoided, with the above-mentioned 45 minute time generally being about the greatest length of time that is commercially acceptable to end users. It is greatly preferred to utilize no more than about 30 minutes, preferably less than 25 minutes, of treatment time, and more preferably the treatment time is in the neighborhood of 20 minutes.

After the above treatment time has elapsed, the aqueous hair treating composition should be removed from the hair in order to prevent further decrease of the strength retention of the treated hair. A major propprotion of the aqueous composition can be removed from the hair by thorough rinsing. It is preferred that the rinsing be followed by a neutralizing step, using any suitable neutralizing agent. A buffered neutralizing shampoo has been found to be effective, but any conventional neutralizing methods and compositions, well known to the art, may be utilized. Preferably the hair is neutralized by reducing the pH thereof to a value of no greater than about 7, and more preferably to a value of about 5.0–6.5. While lower pH values may be used, it is generally preferred to maintain the pH of the treated hair within the range of about 5.0 to about 7.0.

As compared to the compositions described in the earlier above-identified patents, the aqueous hair treating composition produced from the stable composition of the present invention seems to produce a hair relaxing effect faster for equal guanidine hydroxide concentrations. Thus, the guanidine hydroxide concentrations can be reduced while maintaining the same relaxing ability for equal treatment times. In preliminary tests compared to a commercial product produced according to the teachings of the earlier patents, the guanidine hydroxide concentration was reduced from 5.6% to 4.3%, with equal hair relaxing results for equal treatment times and other treatment conditions.

Accelerated stability testing has been conducted on the stable compositions of the present invention. A typical composition can be placed in an oven maintained at 45° C. for one month (generally the art considers that 21 days in a 45° C. oven is equivalent to one year of ambient shelf life) with only a very slight loss of activity and with a slight smell of ammonia noted. The slight loss of activity was so low that it did not impair the resulting relaxing or hair treating ability of the aqueous hair treating compositions made from the stable composition.

ILLUSTRATIVE EXAMPLES

The following is a general breakdown of the ingredients utilized in the present anhydrous relaxer formulation wherein 60 parts of the formulation are mixed with 40 parts of water to obtain guanidine hydroxide.

| GENERAL NAME (CTFA Nomenclature) | TRADE NAME (Supplier) | CONCENTRATION Range in % | PREFERRED CONCENTRATION in % |
|---|---|---|---|
| Liquid Petrolatum (Mineral Oil) | Carnation Mineral Oil (Witco) | 0.05–95.00 | 56.80 |
| Guanidine Carbonate (Guanidine Carbonate) | Guanidine Carbonate (Degussa) | 1.94–84.40 | 7.00 |
| Calcium Oxide (Calcium Oxide) | Calcium Oxide F.C.C. (Missippi Lime) | 0.60–83.06 | 4.11 |
| Polymer JR (Polyquaternium 10) | Polymer JR 30 M (Union Carbide) | 0.05–20.00 | 1.86 |
| Hydroxypropyl Methylcellulose U.S.P. (Hydroxypropyl Methylcellulose) | Polymer XD-1214.44 (Dow Chemical Company) | 0.05–20.00 | 0.83 |
| Glyceryl Tri [12-Hydroxystearate] (Trihydroxystearin) | Additin-70 (Zetes Micro-Tech Corp.) | 0.10–15.00 | 3.00 |
| Titanium Dioxide (Titanium Dioxide) | Unitane 0-220 (American Cyanamid) | 0.0–5.00 | 0.20 |
| Bentone Gel MIO (Mineral Oil (and) Quaternium 18 Hectorite (and) Propylene Carbonate) | Bentone Gel MIO (NL Industries) | 0.10–15.00 | 3.00 |
| Polyoxyethylene (20) Stearyl Ether (Stearth-20) | Brij 78 (ICI Americas) | 1.94–17.56 | 9.00 |
| Polyoxyethylene (2) Stearyl Ether (Steareth-2) | Brij 72 (ICI Americas) | 1.87–12.44 | 8.00 |
| Anhydrous Lanolin (Lanolin) | Super Clearlan (Emery) | 0.0–20.00 | 6.00 |
| Fragrance (Fragrance) | | 0.0–5.0 | 0.20 |

Calcium oxide, (CaO) is preferred over the calcium hydroxide because of its reactivity with free water.

$$CaO + HOH \rightarrow Ca(OH)_2$$

A certain small amount of free water is introduced into the system (anhydrous relaxer) in the raw materials; thus, the raw materials should be carefully selected to minimize the amount of free water introduced. This free water, even in small amounts, can begin a slow conversion of the active ingredients to the guanidinium hydroxide which is not stable for long periods of time at a pH above 11.50. Also, the conversion of this free water with the calcium oxide to form calcium hydroxide puts the water into a state where it is no longer available to convert the active ingredients into guanidinium hydroxide.

The oxides which may be used, besides the calcium oxide, are barium oxide, strontium oxide and mixtures thereof. The criteria for selection of the appropriate oxide to use are the same as for the selection of the hydroxide, namely, that the cation of the oxide form a water-insoluble salt with the anion of the guanidine salt.

Polymer JR 30M is a patented material belonging to Union Carbide Corp. Chemically it is a quaternized polymeric ester of hydroxyethylcellulose and 2-hydroxypropyltrimethylammonium chloride having a molecular weight of approximately 600,000. The Polymer JR 30M, by virtue of its quaternized nature, produces a soft "feel" in the hair and promotes ease of combing. In addition, the Polymer JR 30M functions as a thickening agent for the emulsion formed when the anhydrous formulation is mixed with water. Two additional grades of Polymer JR exist differing from each other and the 30M by their molecular weights. They are the Polymer JR 125 of approximately 250,000 molecular weight and the 400 of approximately 400,000 molecular weight. Either the JR 125 or 400 could be used separately or together in this composition as well as in combination with the JR 30M. However, due to the JR 30M's superior thickening ability, it is preferred.

Other materials which may be used in place of the Polymer JR 30M are Celquat H60 and Celquat L200 from National Starch. The Celquats are quaternized copolymers of hydroxyethylcellulose and diallyldimethylammonium chloride differing only in their molecular weights. The Celquat H60, due to its superior thickening properties, is preferred. The most preferred material is the Polymer JR 30M as it has the needed viscosity building properties in an aqueous medium as well as giving the best conditioning (softest feel and easiest combing) to the hair.

Polymer XD-1214.44 from the Dow Chemical Company is a high molecular weight polymer of hydroxypropylmethylcellulose. It is used also for its ability to thicken the emulsion formed when water is added to the anhydrous composition. The criteria for the selection of a material to function as an emulsion thickener in this application is that the material must be able to solubilize into the aqueous phase at a temperature below 100° F. without producing large lumps and the solubilized thickener must be stable (i.e., exhibit no appreciable viscosity loss) for approximately ten (10) hours.

Additin-70 from Zetes MicroTech Corp. is glyceryl tri [12-hydroxystearate]. It is used as a thickener and stabilizer of the anhydrous composition.

Another material having the same chemical name which may be used in place of the Additin-70 is Thixcin R from NL Chemicals. However, the Additin-70 is preferred due to its narrower particle size distribution resulting in superior viscosity development with less processing time and work at lower concentrations than the Thixcin R.

Unitane 0-220 from American Cyanamid is a cosmetic grade of titanium dioxide. Its purpose in the composition is to give the anhydrous hair treating composition and the emulsion formed, upon the addition of water, a more cosmetically acceptable appearance (lighter in color).

Bentone Gel MIO from NL Chemicals is a condensate product of dihydrogenated tallow dimethyl ammonium chloride and hectorite, a montmorillonite mineral that is the principle constituent of bentonite clay, suspended in mineral oil containing propylene carbonate, a polar additive which promotes, in the presence of high shear, viscosity increase by the condensate product of dihydrogenated tallow dimethyl ammonium chloride and hectorite, otherwise known by its CTFA designation as Quaternium 18 Hectorite. This material aids the Additin-70 in the stabilization of the anhydrous composition, especially with regard to heat.

Brij 78 from ICI Americas is the polyethylene glycol ether of stearyl alcohol having the following formula:

$$CH_3(CH_2)_{16}CH_2(OCH_2CH_2)_nOH$$

where "n" has an average value of 20. This material, in combination with the Brij 72, forms the emulsifier system responsible for producing the cream emulsion produced when water is added to the anhydrous composition. Its HLB number is 15.30±1.00.

Brij 72 from ICI Americas is the polyethylene glycol ether of stearyl alcohol that conforms to the formula:

$$CH_3(CH_2)_{16}CH_2(OCH_2CH_2)_nOH$$

where "n" has an average value of 2. Its HLB number is 4.90±1.00.

Combinations of the Brij 78 and the Brij 72 in such proportions as to produce for the combination an HLB Number within the range of 3 to 17 are preferred. The most preferred being combinations of the Brij 78 and 72 to produce an HLB Number for the combination in the range of 8 to 13 $(CH_3(CH_2)_{10}CH_2\text{-}(OCH_2CH_2)_nOH$ where n=23 as an average).

The Brij 78 was chosen for use over the Brij 35 SP because it produces a much thicker mineral oil and water emulsion in combination with the Brij 72 than did the Brij 35 SP. However, with the use of the appropriate levels of the Polymer XD-1214.44 and the Polymer JR 30M to thicken the emulsion formed when water is added to the anhydrous composition, the Brij 35 SP could be used instead of the Brij 78.

Super Clearlan from Emery Industries is a premium grade of anhydrous lanolin, light in color and low in odor. This material functions as a protective emollient and as a lipophilic hair conditioning agent. Lanolin from other sources will also suffice as long as it is the anhydrous type. The color and odor are of secondary importance as they do not influence the stability nor function of the composition.

Fragrance is used to give both the anhydrous composition and the resulting emulsion, after the addition of water, a more pleasing odor. This material is not essential to the stability or functionality of the composition.

Carnation Mineral Oil from Witco is a liquid mixture of hydrocarbons obtained from petroleum, also known as liquid petrolatum. It has a viscosity of 65 to 75 Saybolt Universal Seconds (S.U.S.) at 100° F. This material's function is that of a protective emollient and as a solvent which is thickened to carry the active ingredients in a dispersed state. Suitable alternatives to the Carnation Mineral Oil must be, as is the Carnation, of a paraffinic type (aliphatic compounds with the empirical formula $C_nH_{2n+2}$ varying from colorless gases through water-white liquids to low-melting point solids). Another paraffinic type mineral oil which may be used in this composition is Dralseol 7 from Penreco.

EXAMPLE 1

A base emollient composition was prepared by melting all of the ingredients listed below at 70° C. and mixing:

|  | Percentage |
| --- | --- |
| Cyclochem NI (Polyethylene Glycol ether of Cetyl Alcohol) | 26.89 |
| Cetyl Alcohol | 6.73 |
| Mineral Oil | 26.89 |
| Petrolatum | 26.89 |
| Propyl Paraben | 0.14 |
| Methyl Paraben | 0.41 |
| Lantrol (Lanolin Oil) | 8.07 |
| Sodium Lauryl Sulfate | 2.02 |
| Stearic Acid | 1.96 |
|  | 100.00 |

To 81.4 parts of the base emollient compostion listed above, 10.6 parts of guanidine carbonate and 8.0 parts of calcium hydroxide were added with mixing to form a stable emollient composition.

To 100 parts of the stable emollient composition, 50 parts of tap water were added and mixed until a white cream was formed, with the white cream relaxer having a pH of 13.4%. The above cream was applied to a swatch of Negro hair, with the hair straightened after cream application. After 15 minutes of contact, the cream compostion was removed by rinsing, and resulting hair maintained it straight configuration.

In a stability test, a jar containing the anhydrous stable relaxer composition was placed in an oven at 110° F. for thirty (30) days (this accelerated aging test is equivalent to more than a year of shelf life). To 50 parts of the oven sample 50 parts of water were added, with the mixture exhibiting a pH of 13.4. A hair swatch test similar to that described above proved that the resulting compostion was still active. Spectrophotometric analysis for guanidine carbonate on the oven sample indicated a loss of 9.5%, and this approximately 10% loss from the original sample was adequate to maintain activity.

EXAMPLE 2

An anhydrous stable relaxer composition was prepared using the procedure of Example 1, with the stable compostion having the following ingredients:

|  | Percentage |
| --- | --- |
| Mineral Oil (Carnation-Witco) | 56.50 |
| Syncrowax HRS-C[(1)] | 7.00 |
| Lanolin, Anhydrous | 6.00 |
| Cetyl Alcohol NF | 5.00 |
| Brij 35 SP | 4.84 |
| Brij 72 | 5.16 |
| Calcium Hydroxide | 6.67 |
| Guanidine Carbonate | 8.83 |
|  | 100.00 |

40 parts of water were added to 60 parts of the anhydrous stable relaxer composition, with the mix exhibiting a pH of 13.5 after thorough mixing. The compostion was applied to the medium to coarse texture, medium length (about 6 inches) hair of an individual in a half-head test vs. the commercial product ("DARK & LOVELY" Hair Relaxer) made in accordance with the disclosures of the U.S. Pat. Nos. 4,304,244 and 4,373,540.

60 parts of the anhydrous stable relaxer composition were mixed with 40 parts of cold tap water and mixed by hand with a flat wooden stick until a smooth cream formed (which took about 40 seconds of mixing time, without undue effort). The resulting aqueous hair treating composition was a cream having a good consistency which was slightly thinner than that of the commercial product. It was noted during the relaxing process that both sides were being relaxed at the same rate. The hair relaxers were washed out and the hair neutralized after 20 minutes of treatment time. The aqueous composition washed out of the hair easier than the commercial product, and had a better "feel", which was somewhat silkier, before neutralization, and after neutralization exhibited a somewhat better "feel" than the commercial product. After neutralization, it was noted that both sides of the head were equally relaxed.

EXAMPLE 3

A stable anhydrous relaxer composition was produced from the following formulation:

|  | Percentage |
| --- | --- |
| Mineral Oil (Carnation-Witco) | 60.75 |
| Syncrowax HRS-C | 6.50 |
| Lanolin-Anhydrous | 6.00 |
| Brij 35 SP | 5.22 |
| Brij 72 | 6.03 |
| Calcium Hydroxide | 6.67 |
| Guanidine Carbonate | 8.83 |
|  | 100.00 |

EXAMPLE 4

A stable anhydrous relaxer composition was produced from the following formulation:

|  | Percentage |
| --- | --- |
| Mineral Oil (Carnation-Witco) | 61.50 |
| Syncrowax HRS-C | 7.00 |
| Lanolin-Anhydrous | 6.00 |
| Brij 35 SP | 4.67 |
| Brij 72 | 5.33 |
| Calcium Hydroxide | 6.67 |
| Guanidine Carbonate | 8.83 |
|  | 100.00 |

EXAMPLE 5

Following the procedure of Example 1, and anhydrous stable relaxer composition was prepared having the following composition:

|  | Percentage |
| --- | --- |
| Mineral Oil (Carnation-Witco) | 61.41 |
| Syncrowax HRS-C | 5.00 |
| Lanolin, Anhydrous | 6.00 |
| Cetyl Alcohol | 5.00 |
| Brij 35 SP | 4.84 |
| Brij 72 | 5.16 |
| Calcium Hydroxide | 5.42 |
| Guanidine Carbonate | 7.17 |
|  | 100.00 |

The above composition was used in a half-head test, in comparison with the "DARK & LOVELY" commercial product. The stable composition was used to provide a composition containing 60 parts of the stable composition and 40 parts of cold tap water. The components were mixed for about 1 minute until a smooth cream was produced, and then immediately half of a subject's coarse texture, with moderate amount of natural curl, medium length (6 to 8 inches), black Negro hair. The commercial product was simultaneously applied to the opposite side of the head. The full head was neutralized with a commercial neutralizing shampoo and conditioned with a commercial protein conditioner, after full relaxation and relaxer removal. The relaxers were washed out at the same time (i.e., 17 minutes after the start of relaxer application). It was noted that the relaxer composition based on the stable composition of the present invention washed out easier than the commercial relaxer composition. A comparison of the hair after the washing out of the relaxer compositions indicated that the hair treated with the aqueous hair treating composition based on the stable composition of the present invention was slightly more lustrous, and had a softer "feel" than the hair on the opposite side of the head. After neutralization, the hair on the two sides of the head appeared to be equal in luster and "feel." There was no noticeable difference in the degree of relaxation between the hair on the different sides of the head.

EXAMPLE 6

Example 5 was repeated, except mineral oil No. 7 (Penreco) was used in place of the Carnation-Witco mineral oil. Similar results were obtained.

It is noted that the commercially available "DARK & LOVELY" hair relaxer product currently utilizes an emulsifier in the relaxer creme portion of the composition which has an HLB number of 5.3. However, the creme is comprised of at least 50% water; therefore, the anhydrous composition of the present invention could not be formulated with the "DARK & LOVELY" product.

What we claim is:

1. An improvement in a composition for treating hair of the type comprising a water-soluble inorganic hydroxide ingredient and a water-soluble guanidine salt ingredient, said ingredients being selected such that reaction products thereof are guanidine hydroxide and a substantially water-insoluble inorganic salt formed by the cation of said inorganic hydroxide ingredient and the anion of said guanidine salt ingredient whereby the reaction producing said guanidine hydroxide will be driven toward completion, the improvement comprising: said hydroxide ingredient and said guanidine salt being incorporated within an effective amount of an anhydrous component which, upon the addition of an effective amount of water to said component, allows said ingredients, upon mixing, to react within said component so as to form guanidine hydroxide which has a pH of at least 11.8 and which is then applied to the hair, said component being an emulsifier.

2. An improvement as claimed in claim 1 wherein said emulsifier has an HLB number ranging from 6.3 to 17.

3. An improvement as claimed in claim 1 wherein said effective amount of said emulsifier ranges from 0.5% to 30% by weight of said composition.

4. An improvement in a method for treating hair of the type comprising the steps of mixing a water-soluble inorganic hydroxide ingredient with a water-soluble guanidine salt ingredient to form guanidine hydroxide having a pH of at least 11.8 and applying said guanidine hydroxide to the hair, the improvement comprising the steps of:
    (a) incorporating, prior to said mixing step, said hydroxide ingredient and said guanidine salt ingredient within an effective amount of an anhydrous component; and
    (b) adding an effective amount of water to said component so that said guanidine hydroxide is formed when said hydroxide ingredient and said guanidine salt ingredient are mixed together within said component.

* * * * *